United States Patent
Itakura et al.

(10) Patent No.: US 7,267,002 B2
(45) Date of Patent: Sep. 11, 2007

(54) CAPACITANCE TYPE PHYSICAL QUANTITY DETECTOR

(75) Inventors: Toshikazu Itakura, Toyota (JP); Toshiki Isogai, Nagoya (JP)

(73) Assignees: DENSO CORPORATION, Kariya (JP); Nippon Soken, Inc., Nishio (JP)

( * ) Notice: Subject to any disclaimer, the term of this patent is extended or adjusted under 35 U.S.C. 154(b) by 68 days.

(21) Appl. No.: 11/185,751

(22) Filed: Jul. 21, 2005

(65) Prior Publication Data

US 2006/0037393 A1 Feb. 23, 2006

(30) Foreign Application Priority Data

Aug. 18, 2004 (JP) .............................. 2004-238727

(51) Int. Cl.
G01R 27/26 (2006.01)
G01N 19/00 (2006.01)

(52) U.S. Cl. .................................. 73/335.03; 324/670

(58) Field of Classification Search ............ 73/335.03, 73/29.02, 335.05; 324/670, 664, 665, 666, 324/667; 338/35

See application file for complete search history.

(56) References Cited

U.S. PATENT DOCUMENTS

| 3,493,855 | A | * | 2/1970 | Norwich | ..................... 324/664 |
| 4,626,774 | A | * | 12/1986 | Regtien | ..................... 324/683 |
| 6,580,600 | B2 | | 6/2003 | Toyoda et al. | |
| 6,867,602 | B2 | * | 3/2005 | Davis et al. | ................. 324/664 |
| 2002/0114125 | A1 | | 8/2002 | Toyoda et al. | |
| 2003/0010119 | A1 | * | 1/2003 | Toyoda | ..................... 73/335.04 |

FOREIGN PATENT DOCUMENTS

| JP | A-5-248976 | 9/1993 |
| JP | A-10-339750 | 12/1998 |

* cited by examiner

Primary Examiner—Michael Cygan
(74) Attorney, Agent, or Firm—Posz Law Group, PLC (57) ABSTRACT

A capacitance type physical quantity detector includes a sensor unit of which the capacitance varies depending upon a change in the physical quantity and a C-V converter unit which converts a change in the capacitance of said sensor unit into a voltage. The C-V converter unit includes an operational amplifier, a feedback capacitor, switching means connected in parallel with said feedback capacitor, a reference voltage-generating circuit for applying a reference voltage to the operational amplifier, and a drive voltage-generating circuit for applying a drive voltage to said sensor unit. At least any one of the feedback capacitance of said feedback capacitor, the reference voltage formed by said reference voltage-generating circuit or the drive voltage formed by said drive voltage-generating circuit varies depending upon the temperature to correct temperature characteristics of the sensor unit.

7 Claims, 7 Drawing Sheets

CAPACITANCE TYPE PHYSICAL QUANTITY DETECTOR

CROSS REFERENCE TO RELATED APPLICATION

This application is based upon, claims the benefit of priority of, and incorporates by reference the contents of, Japanese Patent Application No. 2004-238727 filed on Aug. 18, 2004.

FIELD OF THE INVENTION

The present invention relates to a capacitance type physical quantity detector for detecting physical quantities such as humidity and the like.

BACKGROUND OF THE INVENTION

The present applicant has previously proposed in JP-A-2002-243690 a capacitance type humidity sensor having a moisture-sensitive film of which the specific inductivity varies depending upon the humidity interposed between a pair of electrodes.

The above capacitance type humidity sensor has a sensor unit which comprises a pair of electrodes formed like comb teeth on the same plane of a substrate, and a moisture-sensitive film formed so as to cover the pair of electrodes. Further, in order to detect fine variations in the capacitance maintaining good sensitivity, the above sensor has a C-V converter unit of a switched capacitor constitution. Therefore, when the specific inductivity of the moisture-sensitive film varies accompanying the change in the humidity and the capacitance varies between the pair of electrodes, the change in the capacitance is converted into a voltage through the C-V converter unit and is produced as a sensor output. The humidity is thus detected.

In the above constitution, however, when the moisture-sensitive film interposed between the pair of electrodes exhibits moisture absorbing/releasing properties that vary depending upon the temperature (i.e., temperature characteristics), the temperature characteristics appear in the change of capacitance of the sensor unit, too (temperature characteristics in the sensitivity). Namely, there appears a difference in the characteristics of the sensor output depending upon the temperature.

To correct the temperature characteristics, it can be contrived, for example, to provide a correction circuit for forming an adjusting voltage that varies depending upon the temperature in a stage subsequent to the C-V converter unit to adjust the deviation caused by the temperature characteristics. To form the adjusting voltage having temperature characteristics, however, it is necessary to separately provide a correction circuit portion of a complex circuit constitution, causing an increase in the chip areas and boosting up the cost. It is also possible to correct the temperature characteristics relying upon a complex digital signal processing, boosting, however, the cost, too.

SUMMARY OF THE INVENTION

In view of the above problems, it is an object to provide a capacitance type physical quantity detector of a simple constitution capable of correcting the temperature characteristics of the sensor unit.

In order to achieve the above object, a capacitance type physical quantity detector comprising a sensor unit of which the capacitance varies depending upon a change in the physical quantity, and a C-V converter unit of the switched capacitor constitution which converts a change in the capacitance of the sensor unit into a voltage.

According to a first aspect, the C-V converter unit includes an operational amplifier, a feedback capacitor provided between an input terminal and an output terminal of the operational amplifier, and switching means connected in parallel with the feedback capacitor. The capacitance type physical quantity detector further includes a reference voltage-generating circuit for applying a reference voltage to the non-inverted input terminal of the operational amplifier, and a drive voltage-generating circuit for applying a drive voltage to the sensor unit, wherein at least any one of the feedback capacitance of the feedback capacitor, the reference voltage formed by the reference voltage-generating circuit or the drive voltage formed by the drive voltage-generating circuit is so varied depending upon the temperature as to correct the temperature characteristics of the sensor unit (temperature characteristics of sensitivity).

In the capacitance type physical quantity detector equipped with the C-V converter unit of the switched capacitor constitution that converts a change in the capacitance of the sensor unit into a voltage, the voltage Vs after put to the C-V conversion can be expressed by the following formula, $$Vs = \Delta C / Cf \times V + Vr \tag{1}$$

where $\Delta C$ is the amount of change in the capacitance of the sensor unit due to a change in the physical quantity, $Cf$ is the amount of feedback of the feedback capacitor, $V$ is a drive voltage of the sensor unit, and $Vr$ is a reference voltage applied to the non-inverted input terminal of the operational amplifier.

When the sensor unit has temperature characteristics, $\Delta C$ in the formula (1) varies depending upon the temperature even when there is no change in the physical quantity. According to the present detector, however, at least any one of the feedback capacitance $Cf$ of the feedback capacitor, the reference voltage $Vr$ formed by the reference voltage-generating circuit or the drive voltage $V$ formed by the drive voltage-generating circuit, is varied depending upon the temperature so as to correct the temperature characteristics of the sensor unit. Therefore, there is no need of separately providing the correction circuit portion of a complex constitution in the subsequent stage of the C-V converter unit, and the temperature characteristics of the sensor unit can be corrected relying upon a simple constitution.

Specifically, the feedback capacitor may be constituted by interposing a capacitance-adjusting film having predetermined temperature characteristics between a pair of feedback electrodes that are arranged facing each other and being spaced apart.

In this case, the film for adjusting the capacitance is the one having such temperature characteristics as to correct the temperature characteristics of the sensor unit and of which the specific inductivity does not vary or varies in only a small amount depending upon the change in the physical quantity (humidity).

As the constitution for detecting the humidity, for example, the sensor unit includes a pair of detecting electrodes arranged on the same plane of the substrate facing each other and being spaced apart, a moisture-sensitive film having temperature characteristics provided on the substrate so as to cover the pair of detecting electrodes and to cover the distance between the pair of detecting electrodes, and a pair of reference electrodes arranged on the same plane of the substrate facing each other and being spaced apart, and the feedback capacitor includes a pair of feedback electrodes arranged on the same plane of the substrate facing each other and being spaced apart, and a capacitance-adjusting film provided on the substrate so as to cover the pair of feedback electrodes and to cover the distance between the pair of feedback electrodes.

In the case of the constitution for detecting the humidity, the capacitance-adjusting film may be a moisture-permeating film having moisture-permeating property and predetermined temperature characteristics, or may be a capacitance-adjusting film comprising a moisture-sensitive film having predetermined temperature characteristics and a moisture non-permeating film formed on the moisture-sensitive film and having moisture non-permeating property.

It is desired that the pair of detecting electrodes, pair of reference electrodes and pair of feedback electrodes are provided like comb teeth, respectively. The electrodes in the form of comb teeth make it possible to increase the facing areas and, hence, to increase the amounts of change in the capacitance between the electrodes.

Further, the substrate is a semiconductor substrate having a first insulating film relative to the detecting electrodes, reference electrodes and feedback electrodes, and having a second insulating film between the detecting electrodes and the moisture-sensitive film and between the feedback electrodes and the capacitance-adjusting film.

As the substrate, there can be used an insulating substrate such as a glass substrate. Use of a semiconductor substrate provided with an insulating film enables a semiconductor process to be utilized. This makes it possible to decrease the cost of production. Further, the second insulating film prevents the corrosion on the detection electrodes and on the feedback electrodes.

Further, the reference voltage-generating circuit comprises a variable resistor having a predetermined temperature coefficient and a resistor without temperature dependence, which are connected in series, and a power source voltage is applied across the two resistors to produce a reference voltage as a neutral-point potential that varies depending upon the temperature.

According to this constitution, there can be formed the reference voltage having temperature characteristics despite the simple constitution, and the temperature characteristics of the sensor unit can be corrected.

Further, the drive voltage-generating circuit includes a plurality of variable resistors having different temperature coefficients and selection means for selecting a variable resistor connected to the power source voltage out of the variable resistors based upon a detection signal from the temperature sensor, and a drive voltage that varies depending upon the temperature is produced as the neutral-point potential between the variable resistor selected by the selection means and the resistor without temperature dependency.

As represented by the formula (1), the drive voltage V has a relation ($V=a/\Delta C$ (a: constant)) which is reversely proportional to the temperature characteristics of the sensor unit, i.e., reversely proportional to the temperature characteristics $\Delta C$. Therefore, unlike the feedback capacitance Cf and the reference voltage Vr, the temperature characteristics of the drive voltage V describe a curve. However, the circuit constitution becomes complex if the correction is effected relying on a curve. In the present detector, therefore, a plurality of variable resistors having different temperature coefficients are changed over, and a curve of desired temperature characteristics is approximated by straight lines. This makes it possible to correct the temperature character-istics of the sensor unit relying upon the drive voltage V despite of a simple constitution.

BRIEF DESCRIPTION OF THE DRAWINGS

FIGS. 1A-1B are schematic views illustrating the constitution of a capacitance type humidity sensor according to a first embodiment, wherein

FIGS. 6A-6B are schematic views illustrating the constitution of a feedback capacitor, wherein

FIGS. 7A-7B are illustrations of a modified example of the feedback capacitor, wherein

DESCRIPTION OF THE PREFERRED EMBODIMENTS

A preferred embodiment will now be described with reference to the drawings. In a first embodiment, the capacitance type physical quantity detector is described as a capacitance type humidity sensor.

First Embodiment

Figure 1A:
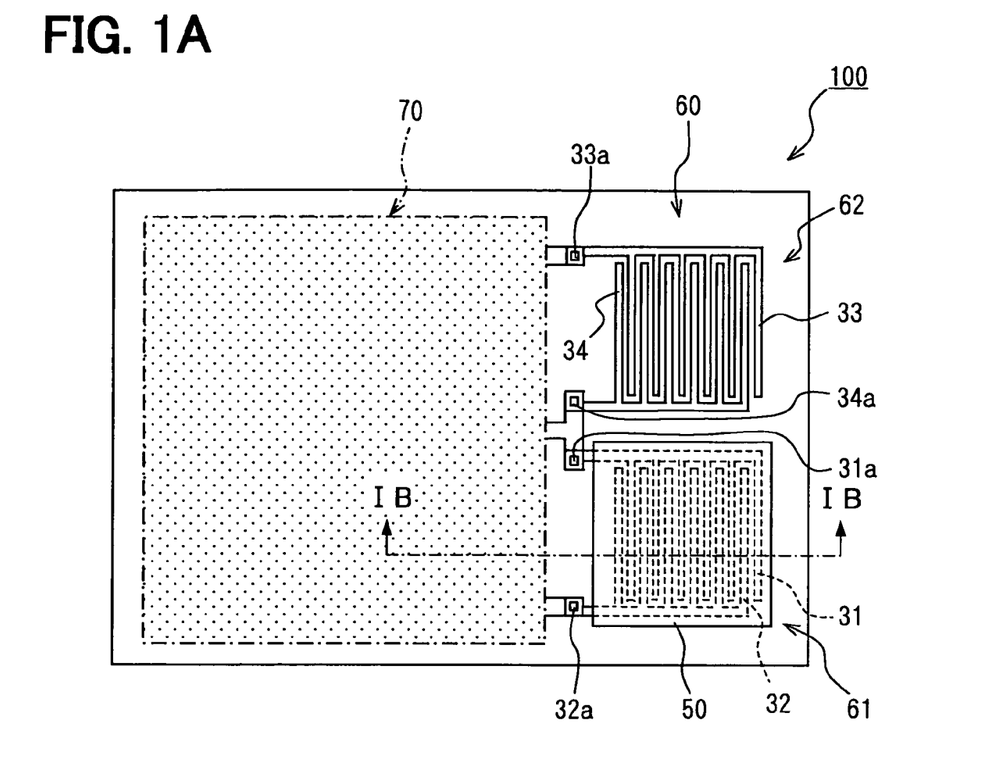
FIG. 1A is a plan view and FIG. 1B is a sectional view along line IB-IB in FIG. 1A.
Figure 1B:
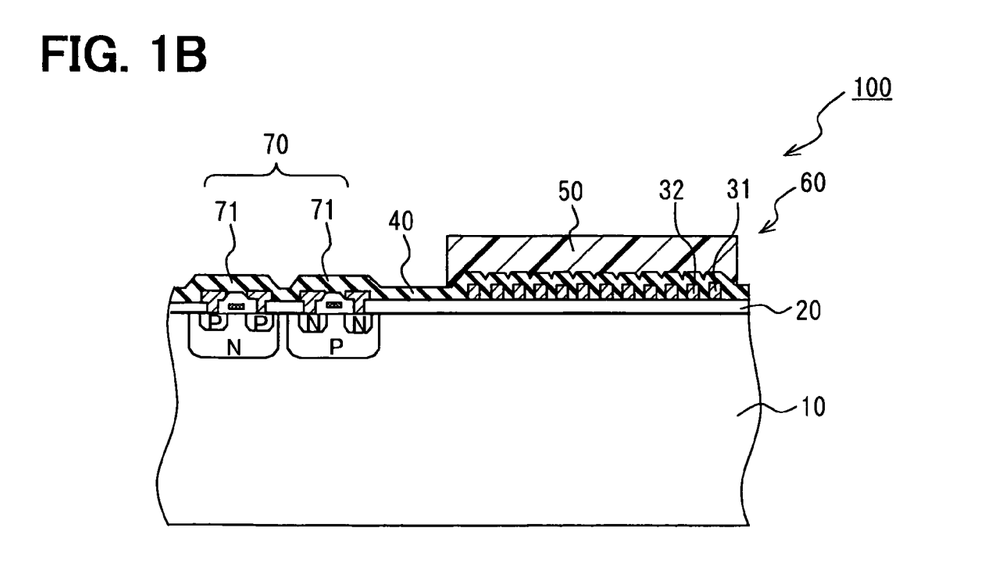

FIG. 1 is a view schematically illustrating the constitution of a capacitance type humidity sensor according to this embodiment, wherein FIG. 1A is a plan view and FIG. 1B is a sectional view along the section IB-IB in FIG. 1A. In FIG. 1A illustrating the sensor unit, the electrodes and wiring are partly illustrated in a see-through manner, and the circuit portion is omitted.

In FIG. 1B, reference numeral 10 denotes a semiconductor substrate which in this embodiment is made of silicon. A silicon oxide film 20 is formed as an insulating film on the upper surface of the semiconductor substrate 10. Further, a pair of detecting electrodes 31 and 32 are arranged on the same plane on the silicon oxide film 20 facing each other and being spaced apart.

There is no particular limitation on the shape of the detecting electrodes 31 and 32. In this embodiment, however, the detecting electrodes 31 and 32 are formed in the shape of comb teeth as shown in FIG. 1A. Employment of the comb teeth shape makes it possible to decrease the area for arranging the detecting electrodes 31, 32 while increasing the areas thereof that are facing each other. This helps increase the amount of change in the capacitance between the detecting electrodes 31 and 32 that vary accompanying the change in the surrounding humidity and, hence, increase the sensitivity of the capacitance type humidity sensor 100.

The detecting electrodes 31 and 32 are formed by depositing a wiring material such as aluminum, copper, gold, platinum or polysilicon on the semiconductor substrate 10 by vaporization or sputtering followed by patterning into a comb teeth pattern relying upon the photolithography processing. In this embodiment, the detecting electrodes 31 and 32 are formed by using aluminum.

Neighboring the detecting electrodes 31 and 32, further, the pair of reference electrodes 33 and 34 are arranged on the same plane on the silicon oxide film 20 facing each other but being spaced apart. The reference electrodes 33 and 34 are formed by using the same material as the detecting electrodes 31 and 32 and in the same pattern.

A silicon nitride film 40 is formed as a protection film on the semiconductor substrate 10 so as to cover the detecting electrodes 31, 32 and the reference electrodes 33, 34. The silicon nitride film 40 is deposited maintaining the same thickness on every portion of the semiconductor substrate 10 by, for example, a plasma CVD method. When the detecting electrodes 31, 32 and the reference electrodes 33, 34 have corrosion resistance against water, however, the protection film (silicon nitride film 40) may not be formed. In FIG. 1A, the silicon nitride film is not shown for convenience.

On the silicon nitride film 40, there is formed a moisture-sensitive film 50 of, for example, a polyimide type polymer having a hygroscopic property so as to cover the detecting electrodes 31, 32 and to cover the distance between the detecting electrodes 31 and 32. The moisture-sensitive film 50 is formed by applying the polyimide type polymer by the spin-coating method or the printing method, followed by heating and curing.

In the thus constituted capacitance type humidity sensor 100, when the water content having a large specific inductivity permeates into the moisture-sensitive film 50, the specific inductivity of the moisture-sensitive film 50 varies depending upon the amount of the water content that has permeated. This causes a change in the capacitance of the capacitor constituted by the detecting electrodes 31, 32 with the moisture-sensitive film 50 as part of the dielectric. The reference electrodes 33 and 34, on the other hand, are not provided with the moisture-sensitive film 50. Therefore, the capacitance of the capacitor constituted by the reference electrodes 33, 34 does not vary or varies only a little. The amount of water content contained in the moisture-sensitive film 50 varies depending upon the ambient humidity of the capacitance type humidity sensor 100. Therefore, the humidity can be detected from a difference between the capacitance across the detecting electrodes 31, 32 and the capacitance across the reference electrodes 33, 34. The portion of the above constitution represents the sensor unit 60, the portion including the detecting electrodes 31, 32 and the moisture-sensitive film 50 represents the detecting unit 61, and the portion including the reference electrodes 33, 34 represents the reference unit 62 of the invention.

Referring to FIG. 1A, the detecting electrodes 31, 32 and the reference electrodes 33, 34 have pads 31a, 32a, 33a, 34a formed at the ends thereof as external connection terminals, and are electrically connected to a circuit portion 70 that includes a C-V converter circuit that will be described later through the pads 31a, 32a, 33a and 34a. As shown in FIG. 1B, the circuit portion 70 is constituted by CMOS transistors 71, and a change in the capacitance of the sensor unit 60 is processed with signals in the circuit portion 70. In FIG. 1A, the circuit portion 70 is hatched for distinction.

In the capacitance type humidity sensor 100 of this embodiment as described above, the circuit portion 70 inclusive of the sensor unit 60 and CMOS transistors 71 is integrated on the same semiconductor substrate 10 to form the capacitance type humidity sensor 100 of a small size. Further, the capacitance type humidity sensor 100 is constituted by a material that can be produced through an ordinary semiconductor production line to realize an inexpensive capacitance type humidity sensor 100.

Figure 2:
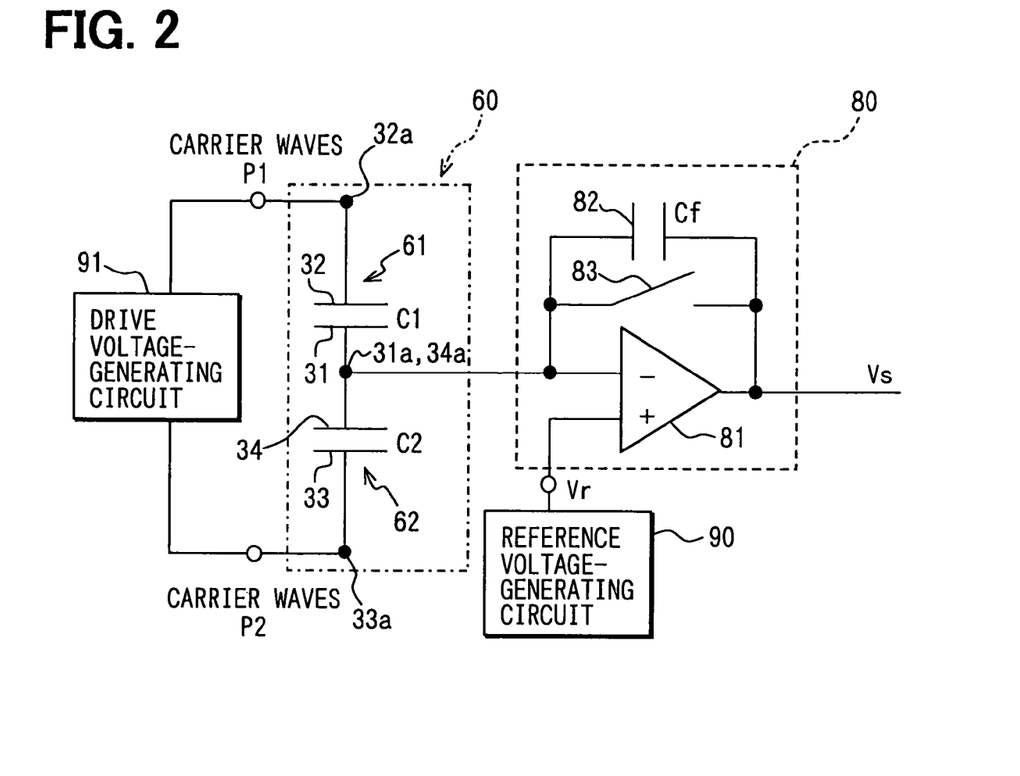
FIG. 2 is a block diagram illustrating a detecting circuit.

Next, FIG. 2 illustrates the detecting circuit in the capacitance type humidity sensor 100 of this embodiment. The circuit portion 70 in the capacitance type humidity sensor 100 of this embodiment includes a C-V converter circuit 80 of the switched capacitor constitution.

The C-V converter circuit 80 is constituted by an operational amplifier 81, a feedback capacitor 82 having a capacitance Cf, and a switch 83. An electrical charge equal to a difference between the electric charge proportional to the capacitance C1 across the detecting electrodes 31, 32 constituting the detecting unit 61 and the electric charge proportional to the capacitance C2 across the reference electrodes 33, 34 constituting the reference unit 62, is accumulated in the feedback capacitor 82 and is converted into a voltage.

The inverted input terminal of the operational amplifier 81 is connected to the detecting electrode 31 and the reference electrode 34 via the pads 31a and 34a. Between the inverted input terminal and the output terminal, there are connected the feedback capacitor 82 and the switch 83 in parallel. Further, a reference voltage-generating circuit 90 is connected to the non-inverted input terminal to apply a reference voltage Vr.

The circuit portion 70, further, has a drive voltage-generating circuit 91 which receives, through the detecting terminal 32 of the detecting unit 61, carrier waves P1 that periodically vary maintaining a predetermined amplitude (0 to V) from the pad 32a, and receives, through the reference electrode 33 of the reference unit 62, the carrier waves P2 having a phase deviated by 180 degrees from the carrier waves P1 and maintaining the same amplitude from the pad 33a.

Figure 3:
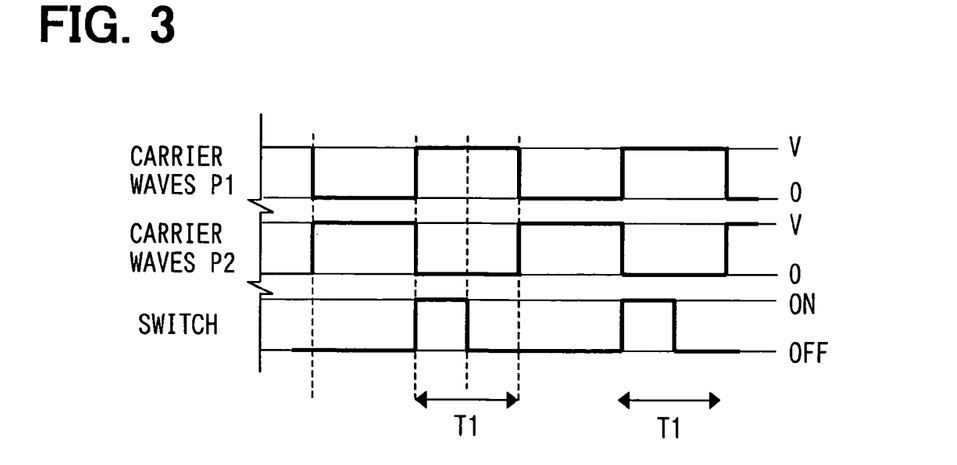
FIG. 3 is a diagram of a timing chart for the detecting circuit.

The switch 83 is turned on/off by a trigger signal formed in synchronism with the clock signals from the drive voltage-generating circuit 91. Referring, for example, to FIG. 3, the switch 83 is set to be turned on for only a predetermined period of time (a time shorter than one-half period of the carrier waves P1) at a rising timing of the carrier waves P1 (breaking timing of the carrier waves P2).

Referring to FIG. 3, when the switch 83 is turned on in the detection period T1, the feedback capacitor 82 is discharged and is reset to the reference voltage Vr. Thereafter, the switch 83 is turned off to end the resetting operation. Next, when the carrier waves P1 and P2 are inverted, an electric charge (C1−C2)×V is released from across the detecting electrodes 31, 32 and from across the reference electrodes 33, 34, and is accumulated in the feedback capacitor 82. FIG. 3 is a diagram of a timing chart for the detecting circuit. Therefore, the output terminal of the operational amplifier 81 produces a voltage Vs depending upon the capacitance difference (C1−C2) of the sensor unit 60 and upon the amplitude V with the reference voltage Vr as a reference. The voltage Vs is given by the following formula, $$Vs = (C1 - C2)/Cf \times V + Vr \qquad (2)$$

In this case, the capacitance C2 of the reference unit 62 does not vary or varies only a little depending upon the change in the surrounding humidity, while the capacitance C1 of the detecting unit 61 varies. Upon detecting the voltage Vs expressed by the formula (2), therefore, the humidity can be detected. The voltage Vs, thereafter, is processed with signals in the signal-processing circuit provided with an amplifier circuit and a low-pass filter, and is detected as a humidity detection signal.

Here, the capacitance is formed by interposing the moisture-sensitive film 50 between the detecting electrodes 31 and 32 as in the capacitance type humidity sensor 100 to detect a change in the capacitance caused by a change in the specific inductivity of the moisture-sensitive film 50. Therefore, when the moisture absorbing/releasing properties of the moisture-sensitive film 50 (i.e., temperature characteristics) differ depending upon the temperature, there also appear temperature characteristics (temperature characteristics of sensitivity) in the change in the capacitance of the detecting unit 61, too, i.e., in the change in the capacitance of the sensor unit 60, too. In this case, a difference occurs in the characteristics of the sensor output depending upon the temperature.

Figure 4:
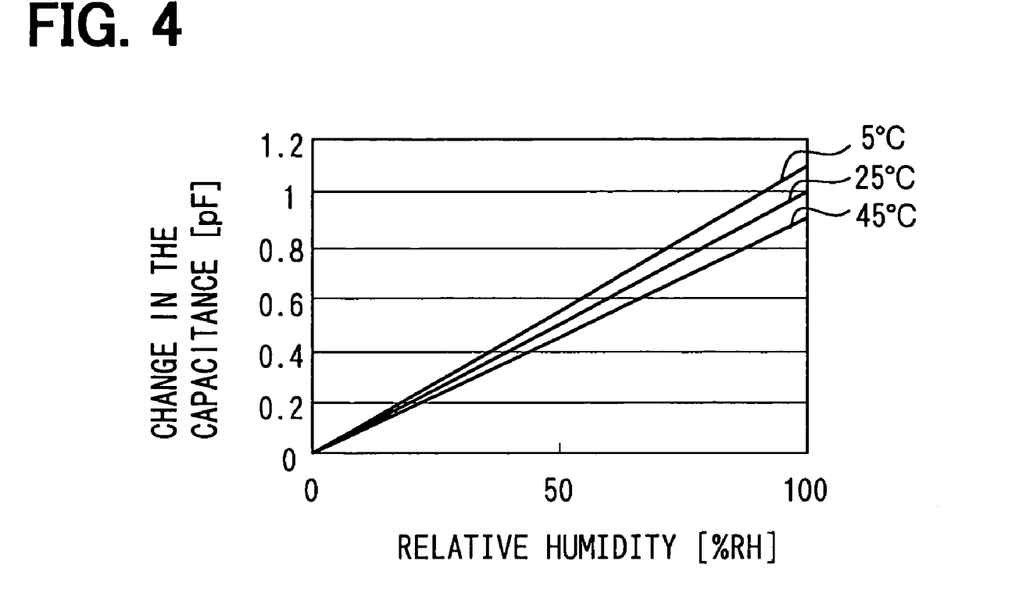
FIG. 4 is a diagram illustrating the temperature characteristics of a sensor unit.

Referring, for example, to FIG. 4, the sensor unit 60 exhibits a change of capacitance of 1 pF at 25° C. depending upon a change of from 0% RH to 100% RH, and temperature characteristics of 5000 ppm/° C. (i.e., 0.1 pF/20° C.). In this case, if Cf=5.0 pF, Vr=2.5 V and V=5.0 V, changes in the capacitance at, for example, 5° C. and 45° C. are 0.1 pF relative to that of 25° C. at 100% RH. FIG. 4 is a diagram illustrating the temperature characteristics of the sensor unit 60.

Figure 5:
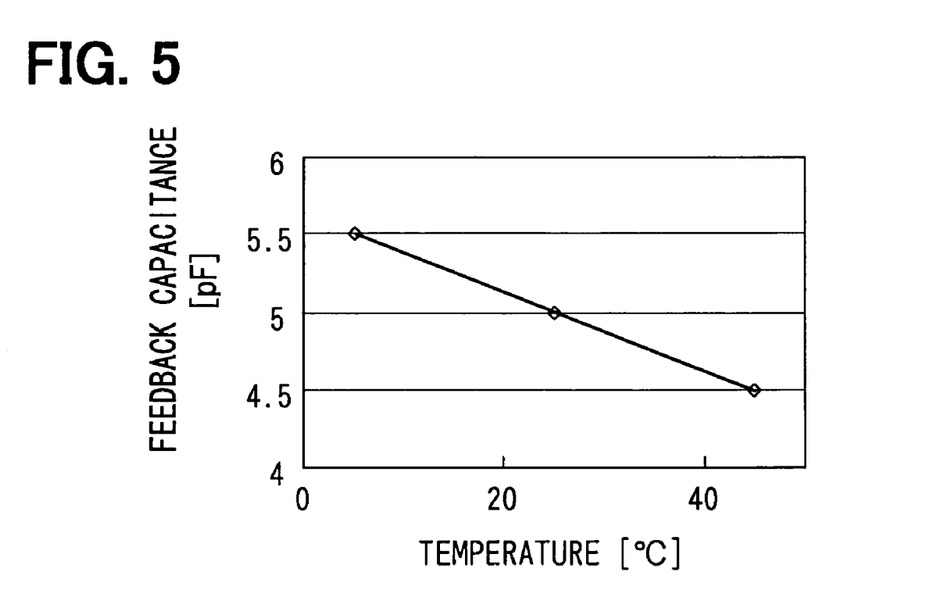
FIG. 5 is a diagram illustrating the temperature characteristics of a feedback capacitor for correcting the temperature characteristics of the sensor unit.

According to this embodiment, therefore, the temperature characteristics of the sensor unit 60 are corrected by the feedback capacitance Cf of the feedback capacitor 82 that constitutes the C-V converter circuit 80. To correct the temperature characteristics of the sensor unit 60 shown in FIG. 4, for example, the temperature characteristics of 0.5 pF/20° C. may be imparted to the feedback capacitance Cf from the relationship of the formula 2 as shown in FIG. 5. FIG. 5 is a diagram illustrating the temperature characteristics of the feedback capacitance Cf for correcting the temperature characteristics of the sensor unit 60.

Concretely, to impart predetermined temperature characteristics to the feedback capacitance Cf, the feedback capacitor 82 is constituted by interposing a capacitance-adjusting film having predetermined temperature characteristics between a pair of feedback electrodes arranged facing each other and being spaced apart. As the capacitance-adjusting film, it is desired to use the one having such temperature characteristics that correct the temperature characteristics of the sensor unit 60, and of which the specific inductivity does not vary or varies only a little despite of change in the humidity.

Figure 6A:
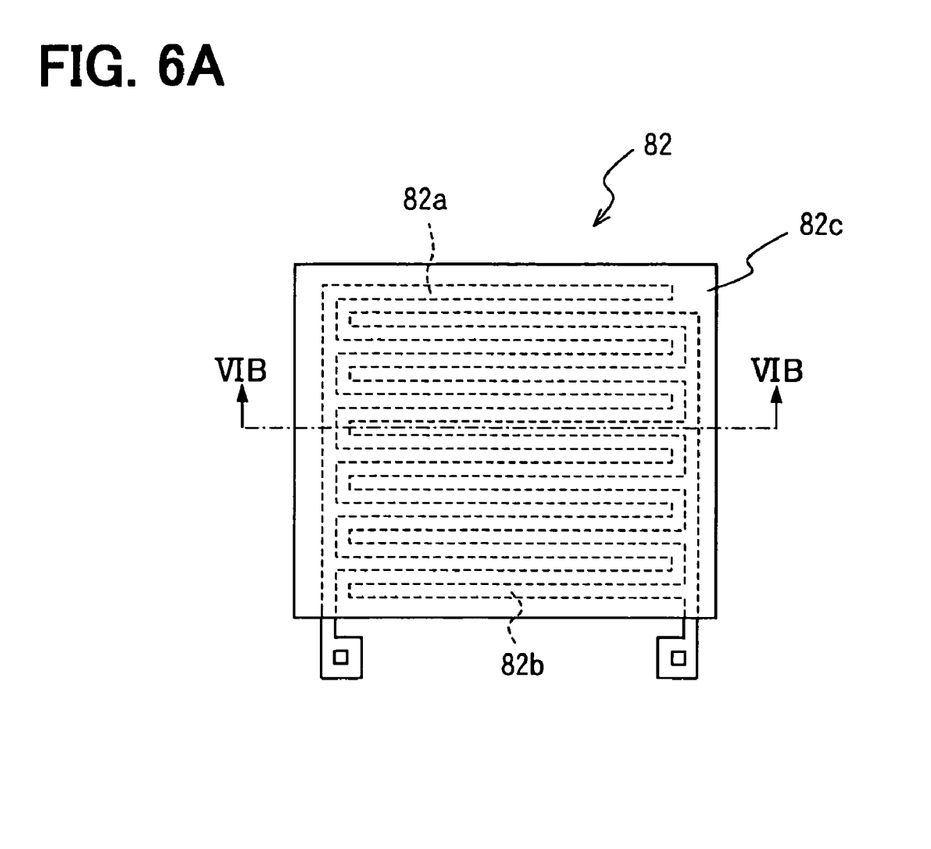
FIG. 6A is a plan view and FIG. 6B is a sectional view along the section VIB-VIB in FIG. 6A.
Figure 6B:
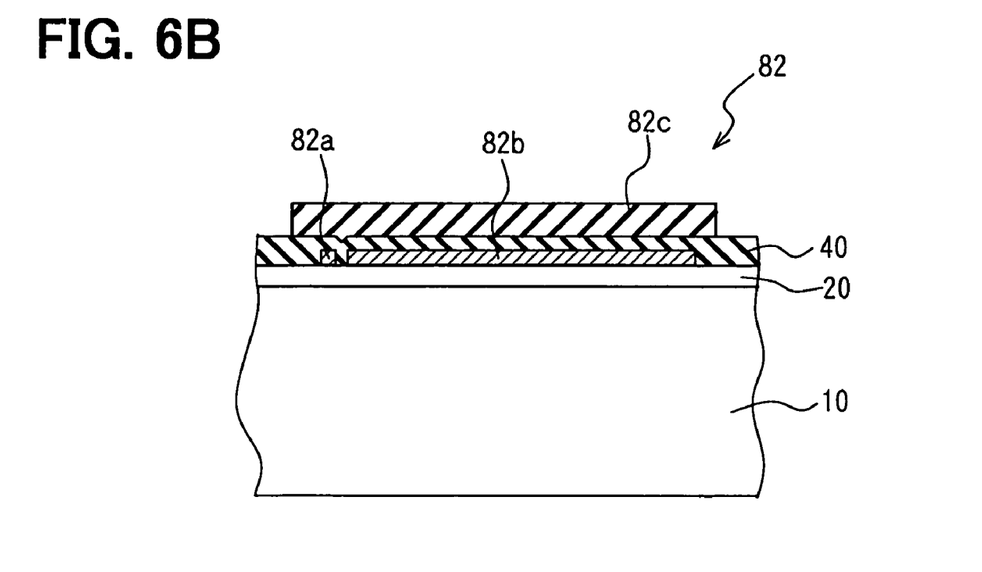

Referring to FIGS. 6A and 6B, the feedback electrodes 82A and 82B of this embodiment are arranged on the same plane on a silicon oxide film 20 facing each other and being spaced apart. FIG. 6 is a view schematically illustrating the constitution of the feedback capacitor 82, wherein FIG. 6A is a plan view and FIG. 6B is a sectional view along the section VIB-VIB in FIG. 6A. The feedback electrodes 82A and 82B are made of the material same as that of the detecting electrodes 31, 32 and are formed in the same pattern. Further, the silicon nitride film 40 is formed as a protection film on the semiconductor substrate 10 so as to cover the feedback electrodes 82A and 82B. On the silicon nitride film 40, there is further formed a moisture-permeating film 82c of, for example, a silicon gel as a capacitance-adjusting film to cover the feedback electrodes 82a, 82b and to cover the distance between the feedback electrodes 82a and 82b.

The moisture-permeating film 82c has been so adjusted as to possess predetermined temperature characteristics yet maintaining moisture-permeating property, and the feedback capacitance Cf so varies depending upon the temperature as to offset the temperature characteristics of the sensor unit 60.

Therefore, the capacitance type humidity sensor 100 of this embodiment is the one in which the feedback capacitor 82 constituting the C-V converter circuit 80 is simply provided with a moisture-permeating film 82c having temperature characteristics relying upon a semiconductor process for forming the sensor 100. Therefore, despite a simple analog constitution, the sensor 100 corrects the temperature characteristics (temperature characteristics of sensitivity) of the sensor unit 60.

In this embodiment, in particular, the moisture-sensitive film 50 is simply replaced by the moisture-permeating film 82c in the constitution of the detecting unit 61 enabling the constitution to be simplified.

Figure 7A:
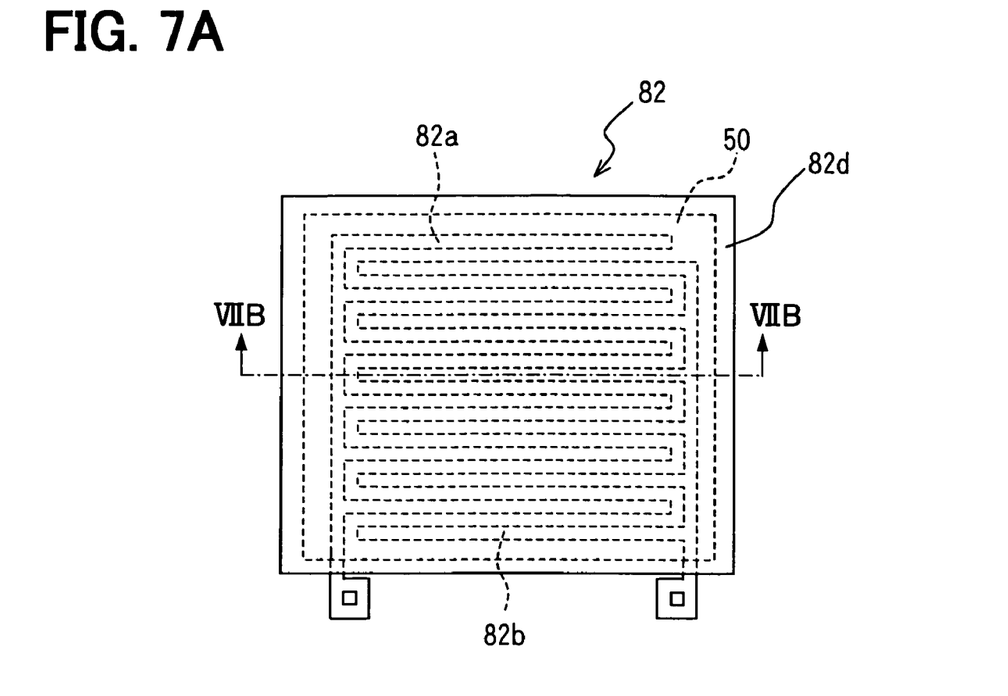
FIG. 7A is a plan view and FIG. 7B is a sectional view along the section VIIB-VIIB of FIG. 7A.
Figure 7B:
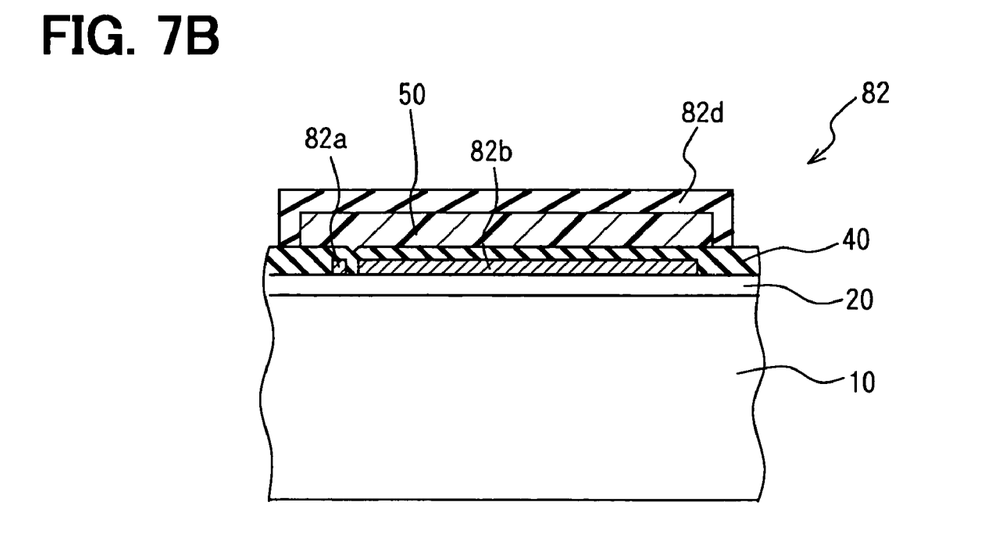

The capacitance-adjusting film is not limited to the moisture-permeating film 82c only. As shown in, for example, FIGS. 7A and 7B, the capacitance-adjusting film may be constituted by the moisture-sensitive film 50 which is so provided as to cover the feedback electrodes 82a, 82b and to cover the distance between the feedback electrodes 82a and 82b, and a moisture non-permeating film 82d formed on the moisture-sensitive film 50 and having moisture non-permeating property. In this case, the moisture-sensitive film 50 which causes the sensor unit 60 to possess temperature characteristics is covered with the moisture non-permeating film 82d which is, for example, a silicon oxide film or a silicon nitride film (silicon nitride film in this embodiment) so that the feedback capacitance Cf will not be varied by the humidity. Therefore, this makes it possible to more accurately correct the temperature characteristics. As the moisture-sensitive film that constitutes the feedback capacitor 82, there may be used the one that is different from the moisture-sensitive film 50 in the detecting unit 61. By using the same films, however, the temperature characteristics become the same, and the constitution can be simplified giving advantage.

Second Embodiment

Figure 8:
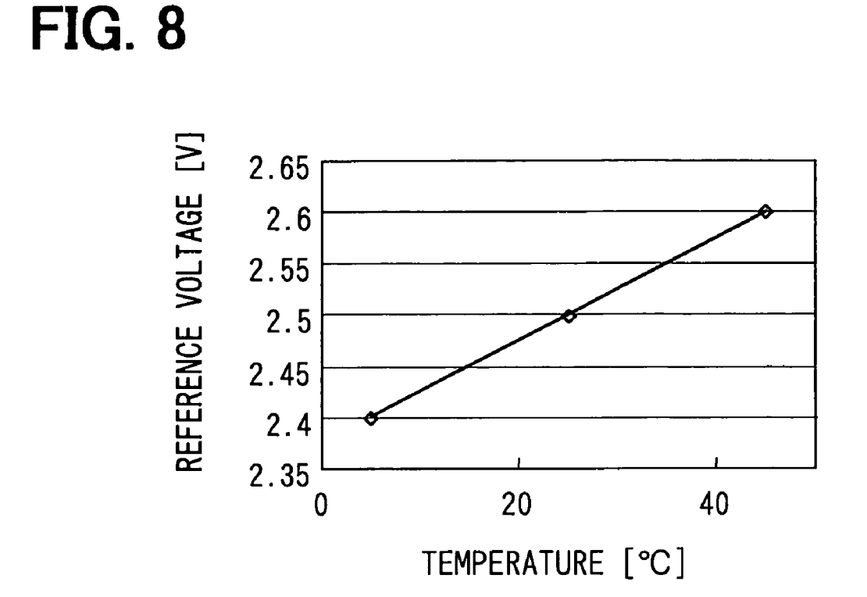
FIG. 8 is a diagram illustrating the temperature characteristics of the reference voltage for correcting the temperature characteristics of the sensor unit according to a second embodiment.
Figure 9:
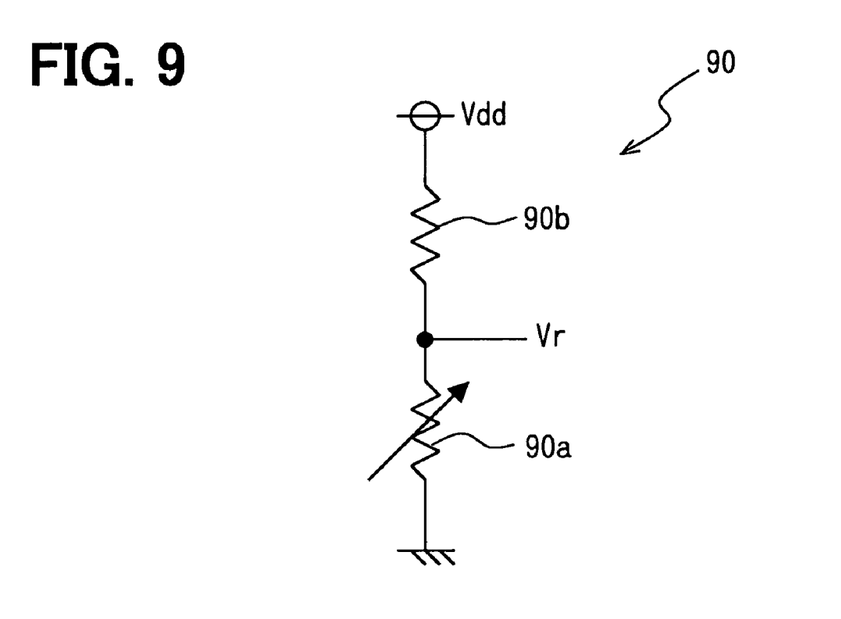
FIG. 9 is a diagram illustrating the constitution of a reference voltage-generating circuit.

Next, a second embodiment will be described with reference to FIGS. 8 and 9. FIG. 8 is a diagram illustrating the temperature characteristics of the reference voltage for correcting the temperature characteristics of the sensor unit 60 shown in FIG. 4, and FIG. 9 is a diagram illustrating the constitution of the reference voltage-generating circuit 90 for imparting predetermined temperature characteristics to the reference voltage Vr.

The capacitance type humidity sensor 100 of the second embodiment is largely common to that of the first embodiment. Therefore, common portions are not described in detail but different portions are described in detail.

The second embodiment is different from the first embodiment with respect to that the temperature characteristics of the sensor unit 60 are corrected by the reference voltage Vr.

In this embodiment, the temperature characteristics of the sensor unit 60 are corrected by the reference voltage Vr applied to the non-inverted input terminal of the operational amplifier 81 that constitutes the C-V converter circuit 80. In order to correct the temperature characteristics of the sensor unit 60 shown in, for example, FIG. 4 of the first embodiment, the temperature characteristics of 0.1 V/20° C. may be imparted to the reference voltage Vr from the relationship of the formula 2 as shown in FIG. 8.

Concretely, as shown in FIG. 9, the reference voltage-generating circuit 90 for generating the reference voltage Vr is constituted by connecting a variable resistor 90a having a predetermined temperature coefficient and a resistor 90b without temperature dependency in series. A power source voltage Vdd is applied across the two resistors 90a and 90b to form the reference voltage Vr which is a neutral-point potential that varies depending upon the temperature.

As described above, the capacitance type humidity sensor 100 of this embodiment, although having a simple construction, is also capable of correcting the temperature characteristics of the sensor unit 60 (temperature characteristics of sensitivity).

The resistor 90b is not limited to the one without temperature dependency. Even if the resistor 90b has a temperature dependency different from that of the resistor 90a, a difference in the temperature coefficient can be maintained between the resistors 90a and 90b to impart temperature dependency to the neutral-point potential.

Third Embodiment

Figure 10:
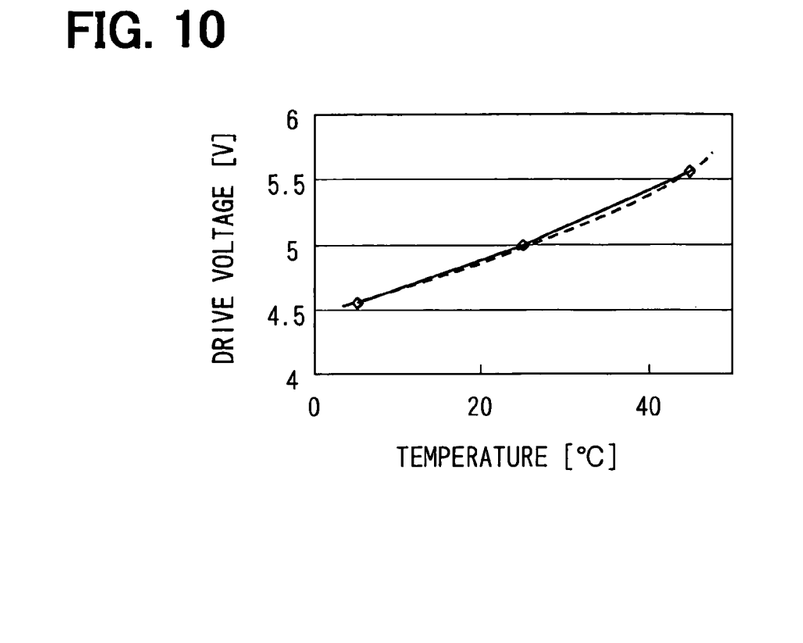
FIG. 10 is a diagram illustrating the temperature characteristics of the drive voltage for correcting the temperature characteristics of the sensor unit according to a third embodiment.
Figure 11:
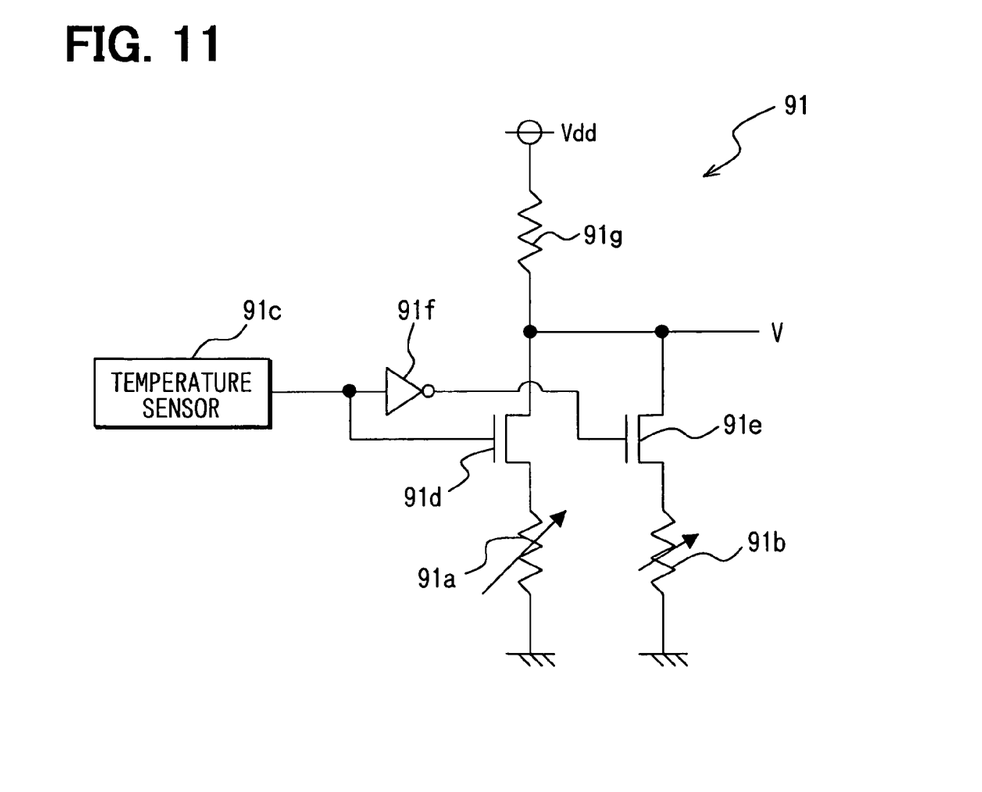
FIG. 11 is a diagram illustrating the constitution of a drive voltage-generating circuit.

Next, a third embodiment will be described with reference to sectional views of FIGS. 10 and 11 illustrating the capacitance type humidity sensor 10. FIG. 10 is a diagram illustrating the temperature characteristics of the drive voltage for correcting the temperature characteristics of the sensor unit 60 shown in FIG. 4, and FIG. 11 is a diagram illustrating the constitution of a drive voltage-generating circuit 91 for imparting predetermined temperature characteristics to the drive voltage V.

The capacitance type humidity sensor 100 of the third embodiment is largely common to that of the first embodiment. Therefore, common portions are not described in detail but different portions are described in detail.

The third embodiment is different from the first embodiment with respect to that the temperature characteristics of the sensor unit 60 are corrected by the drive voltage V.

In this embodiment, the temperature characteristics of the sensor unit 60 are corrected by the drive voltage V (carrier waves P1, P2) applied to the sensor unit 60. From the relationship of the formula 2, however, the drive voltage has a reversely proportional relationship (V=a/$\Delta$C (a: constant)) relative to the temperature characteristics of the capacitance change $\Delta$C (C1−C2). Unlike the feedback capacitance Cf and the reference voltage Vr, therefore, the temperature characteristics of the drive voltage V become as represented by a curve (indicated by a broken line) shown in FIG. 10.

If it is attempted to effect the correction using the curve, therefore, the constitution of the drive voltage-generating circuit 91 becomes complex. According to this embodiment as shown in FIG. 10, therefore, a curve of desired temperature characteristics is approximated by connecting straight lines (solid lines in the drawing) having different inclinations, in order to correct the temperature characteristics of the sensor unit 60 relying upon a simple constitution.

Concretely as shown in FIG. 11, the drive voltage-generating circuit 91 for forming the drive voltage V is constituted by a plurality of variable resistors 91a, 92b having different temperature coefficients, and selection means 91d to 91f for selecting the variable resistor 91a, 91b that is to be connected to the power source voltage Vdd out of the plurality of variable resistors 91a, 91b based on a sensor signal from the temperature sensor 91c. The drive voltage V that varies depending upon the temperature is produced as a neutral-point potential between a resistor 91g without temperature dependency and the variable resistor 91a (91b) selected by the selection means 91d to 91f.

More concretely, the temperature sensor 91c sends, to the selection means 91d to 91f, a LOW signal when the temperature is lower than a predetermined value and a HI signal when it is high, so that the connection of the resistor 91g to the two variable resistors 91a, 91b is changed over with a predetermined temperature as a boundary. The selection means includes two transistors 91d and 91e, and an inverter 91f. The sensor signal is directly transmitted to the transistor 91d that is connected to the variable resistor 91a, and a signal inverted through the inverter 91f (e.g., the HI signal is outputted when the LOW signal is received) is transmitted to the transistor 91e connected to the variable resistor 91b. Therefore, when the sensor signal of the temperature sensor 91c is the LOW signal, the transistor 91d is turned off and the transistor 91e is turned on. That is, the power source voltage Vdd is applied between the variable resistor 91b and the resistor 91g, and the neutral-point potential is output as the drive voltage V. When the sensor signal of the temperature sensor 91c is the HI signal, the transistor 91d is turned on and the transistor 91e is turned off. That is, the power source voltage Vdd is applied between the variable resistor 91a and the resistor 91g, and the neutral-point potential is output as the drive voltage V. Accordingly, the curve of desired temperature characteristics can be approximated by connecting straight lines of different inclinations with the predetermined temperature as a boundary.

As described above, the capacitance type humidity sensor 100 of this embodiment, is capable of correcting the temperature characteristics of the sensor unit 60 (temperature characteristics of sensitivity) despite having a simple construction.

This embodiment has dealt with an example of approximation by straight lines by changing over the two variable resistors 91a and 91b. However, the number of the variable resistors is not limited to two only.

In this embodiment, too, even when the resistor 91g has a temperature dependency different from those of the variable resistors 91a and 91b like the resistor 90b of the second embodiment, a difference in the temperature coefficient can be maintained between the resistors 91a and 91g (or between the resistors 91b and 91g) enabling the neutral-point potential to possess temperature dependency.

Though preferred embodiments of the invention were described above, the invention is in no way limited to the above embodiments only but can be put into practice being varied in a variety of ways.

This embodiment has dealt with the capacitance type humidity sensor 100 that detects the humidity based on a change in the capacitance as the capacitance type physical quantity detector. In addition to the above, however, the invention can be further applied to the one so constituted as to detect the physical quantities such as the acceleration, angular velocity or pressure based on a change in the capacitance, equipped with the C-V converter circuit 80 of the switched capacitor constitution for converting the change in the capacitance into a voltage, and with the sensor output varying depending upon the temperature.

This embodiment has dealt with an example of using the semiconductor substrate 10 of silicon as a substrate, and forming the detecting electrodes 31, 32, reference electrodes 33, 34 and feedback electrodes 82a, 82b on the semiconductor substrate 10 through the silicon nitride film 20. By using the semiconductor substrate 10 as the substrate, as described above, the capacitance type humidity sensor 100 can be formed relying upon a generally employed semiconductor process decreasing the cost of production. As the substrate, however, there can further used an insulating substrate such as a glass substrate.

There was further described an example of forming the moisture-sensitive film 50 on the silicon nitride film 40 which is the protection film. When the silicon nitride film 40 is not formed, however, the humidity-sensitive film 50 can be formed on the silicon oxide film 20. When the substrate is an inorganic insulating substrate such as a glass substrate, further, the moisture-sensitive film 50 can be directly formed on the insulating substrate.

Further, the embodiment has dealt with an example where the detection electrodes 31, 32, reference electrodes 33, 34, and feedback electrodes 82a, 82b were of the comb teeth structure. However, the electrodes forming the capacity are not limited to those of the above structure only. There may be employed, for instance, the electrodes of the so-called parallel flat plate type.

The embodiment has dealt with an example in which the temperature characteristics of the sensor unit 60 were corrected by any one of the feedback capacitance Cf, reference voltage Vr or drive voltage V. However, the temperature characteristics of the sensor unit 60 may be corrected by the feedback capacitance Cf, reference voltage Vr and drive voltage V in combination.

Moreover, the constitutions of the reference voltage-generating circuit 90 and the drive voltage-generating circuit 91 are not limited to only those that were described above.

The invention claimed is:

1. A capacitance type physical quantity detector comprising:
   a sensor unit of which the capacitance varies depending upon a change in the physical quantity; and
   a C-V converter unit of the switched capacitor constitution which converts a change in the capacitance of said sensor unit into a voltage, wherein
   said C-V converter unit includes an operational amplifier, a feedback capacitor provided between an input terminal and an output terminal of said operational amplifier, and switching means connected in parallel with said feedback capacitor,
   said capacitance type physical quantity detector further includes a reference voltage-generating circuit for applying a reference voltage to the non-inverted input terminal of said operational amplifier, and a drive voltage-generating circuit for applying a drive voltage to said sensor unit,
   at least any one of the feedback capacitance of said feedback capacitor, the reference voltage formed by said reference voltage-generating circuit or the drive voltage formed by said drive voltage-generating circuit so varies depending upon the temperature as to correct the temperature characteristics of said sensor unit,
   said feedback capacitor is constituted by interposing a capacitance-adjusting film having predetermined temperature characteristics between a pair of feedback electrodes that are arranged facing each other and being spaced apart,
   said sensor unit includes a pair of detecting electrodes arranged on the same plane of a substrate facing each other and being spaced apart, a moisture-sensitive film having temperature characteristics provided on the substrate so as to cover said pair of detecting electrodes and to cover the distance between said pair of detecting electrodes, and a pair of reference electrodes arranged on the same plane of said substrate facing each other and being spaced apart, and
   said feedback capacitor includes a pair of said feedback electrodes arranged on the same plane of said substrate facing each other and being spaced apart, and said capacitance-adjusting film provided on said substrate so as to cover said pair of feedback electrodes and to cover the distance between said pair of feedback electrodes.

2. A capacitance type physical quantity detector according to claim 1, wherein said capacitance-adjusting film is a moisture-permeating film having predetermined temperature characteristics.

3. A capacitance type physical quantity detector according to claim 1, wherein said capacitance-adjusting film is constituted by said moisture-sensitive film and a moisture non-permeating film provided on said moisture-sensitive film.

4. A capacitance type physical quantity detector according to claim 1, wherein said pair of detecting electrodes, said pair of reference electrodes and said pair of feedback electrodes are provided in the shape of comb teeth, respectively.

5. A capacitance type physical quantity detector according to claim 1, wherein said substrate is a semiconductor substrate having a first insulating film relative to said detecting electrodes, said reference electrodes and said feedback electrodes, and having a second insulating film between said detecting electrodes and said moisture-sensitive film and between said feedback electrodes and said capacitance-adjusting film.

6. A capacitance type physical quantity detector according to claim 1, wherein said reference voltage-generating circuit comprises a variable resistor having a predetermined temperature coefficient and a resistor without temperature dependency, which are connected in series, and a power source voltage is applied across the two resistors to form a reference voltage as a neutral-point potential that varies depending upon the temperature.

7. A capacitance type physical quantity detector according to claim 1, wherein said drive voltage-generating circuit includes a plurality of variable resistors having different temperature coefficients and selection means for selecting a variable resistor connected to the power source voltage out of said variable resistors based upon a detection signal from the temperature sensor, and said drive voltage that varies depending upon the temperature is produced as the neutral-point potential between said variable resistor selected by said selection means and the resistor without temperature dependency.

* * * * *